(12) United States Patent
Scarfi

(10) Patent No.: US 6,458,129 B2
(45) Date of Patent: Oct. 1, 2002

(54) MEDICAL INSTRUMENT FOR CUTTING TISSUE IN THE HUMAN OR ANIMAL BODY

(76) Inventor: Andrea Scarfi, Heldelfinger Strasse 148, D-73760 Ostfildern (DE)

(*) Notice: Subject to any disclaimer, the term of this patent is extended or adjusted under 35 U.S.C. 154(b) by 0 days.

(21) Appl. No.: 09/849,082

(22) Filed: May 4, 2001

Related U.S. Application Data

(63) Continuation of application No. PCT/EP99/08483, filed on Nov. 5, 1999.

(30) Foreign Application Priority Data

| Nov. 5, 1998 | (DE) | 198 51 006 |
| Feb. 2, 1999 | (DE) | 199 04 055 |
| Jul. 22, 1999 | (DE) | 199 34 536 |
| Oct. 30, 1999 | (DE) | 199 53 141 |

(51) Int. Cl.[7] .............................. A61B 18/18
(52) U.S. Cl. ..................... 606/50; 606/45; 606/174
(58) Field of Search ................. 606/41, 45, 46, 606/48–52, 167, 170, 207, 174; 7/135; D24/147

(56) References Cited

U.S. PATENT DOCUMENTS

| 2,127,190 | A | | 8/1938 | Solomon |
| 4,452,106 | A | | 6/1984 | Tartaglia |
| 5,456,684 | A | * | 10/1995 | Schmidt et al. ............ 604/35 |
| 5,509,923 | A | | 4/1996 | Middleman et al. |
| 5,637,111 | A | * | 6/1997 | Sutcu et al. ............ 606/174 |
| 5,908,420 | A | * | 6/1999 | Parins et al. ............ 606/170 |
| 5,922,008 | A | * | 7/1999 | Gimpelson ............ 606/207 |

FOREIGN PATENT DOCUMENTS

| CH | 186 088 | 8/1936 |
| DE | 195 44 523 | 6/1997 |

* cited by examiner

Primary Examiner—Michael Peffley
(74) Attorney, Agent, or Firm—St. Onge Steward Johnston & Reens LLC

(57) ABSTRACT

A medical instrument is provided for cutting tissue or vessels in the human or animal body. The instrument comprises two scissor arms pivotal with respect to one another, each having a cutting edge. The cutting edges slide across one another when the scissor arms are pivoted. The first and second scissor arms are configured as electrodes to be supplied with high frequency current and pivotal about a stationary pivot axis arranged at the scissor arms. At least one of the scissor arms comprises at least one bracket connected thereto, which at least partially extends over the outer side of the other scissor arm.

12 Claims, 4 Drawing Sheets

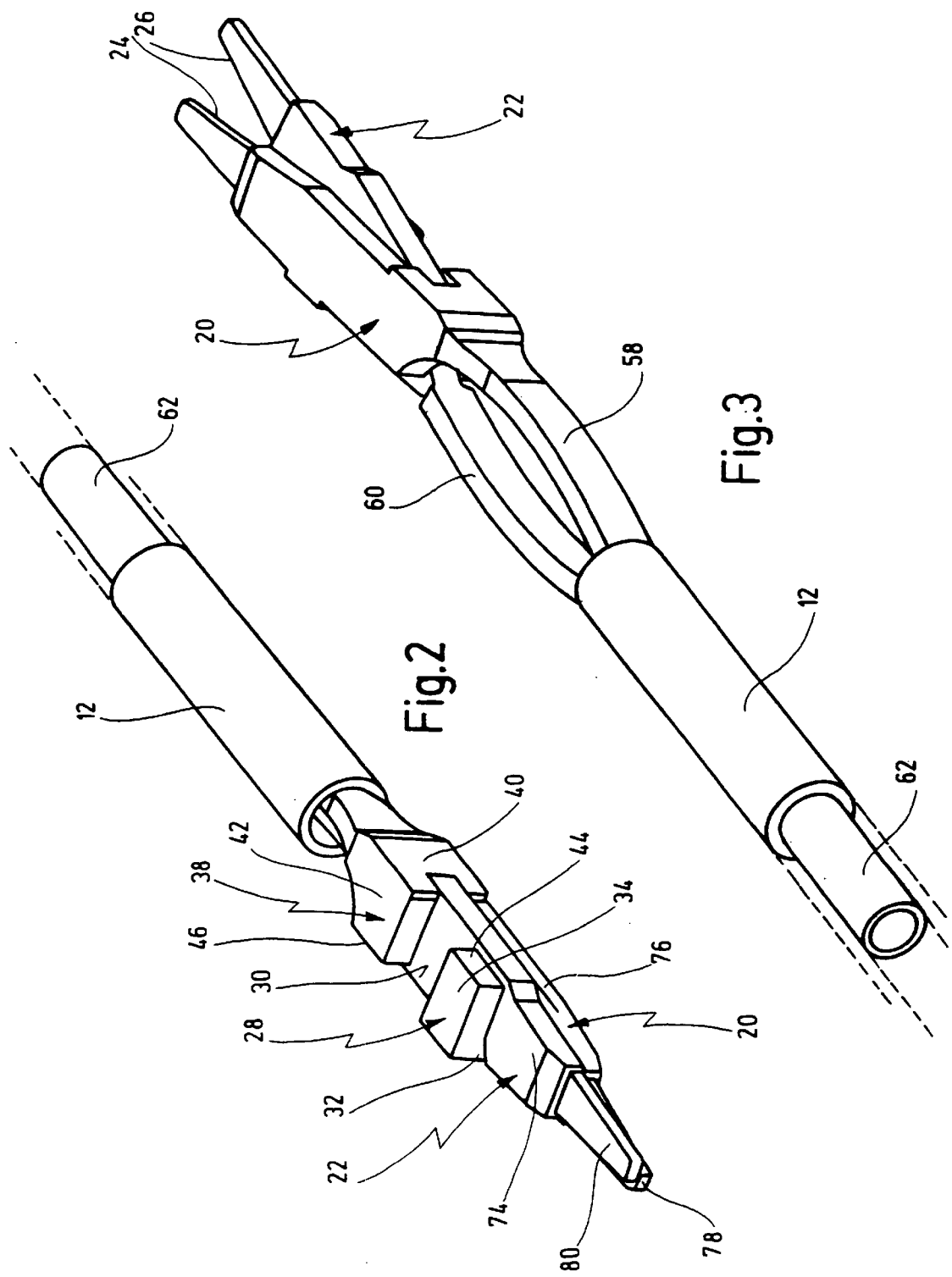

MEDICAL INSTRUMENT FOR CUTTING TISSUE IN THE HUMAN OR ANIMAL BODY

CROSS REFERENCE TO PENDING APPLICATION

This application is a continuation of pending International application PCT/EP 99/08483 filed on Nov. 5, 1999, which designates the United States, and which claims priority of German patent applications DE 198 51 006 filed on Nov. 5, 1998; DE 199 04 055 filed on Feb. 2, 1999; DE 199 34 536 filed on Jul. 22, 1999; and DE 199 53 141 filed on Oct. 30, 1999.

GROUND OF THE INVENTION

The invention relates to a medical instrument for cutting and bipolar coagulating tissue in the human or animal body.

Such an instrument is disclosed in DE 197 00 605 A1. Such instruments are used in minimally invasive surgery for cutting tissue in human or animal bodies. The known instrument of DE 197 00 605 A1 comprises scissor arms spread apart to opposing sides which are pivotal with respect to one another. Each scissor arm comprises a cutting edge where the cutting edges slide across one another when pivoting the scissor arms. Tissue is to be mechanically cut with this configuration of the scissor arms.

The scissor arms each comprise a bending portion at their proximal ends over which a slide tube can be slid by actuating a handle at the proximal end of the instrument. This causes the scissor arms to be urged radially toward one another out of their spread position for cutting tissue. When retracting the slide tube, the scissor arms are resiliently spread apart. Such an actuating mechanism for medical pincers is also disclosed in U.S. Pat. No. 5,334,198.

In a first embodiment of the above-mentioned instrument, the scissor arms are configured without a linkage, i.e. the scissor arms are not connected to one another and are also not otherwise guided during the pivot motion. Because of this, the pivoting arms are spread or bent transversely to the axial direction of the scissor arms, especially for hard tissue, for example vessels. The shearing effect of the two cutting edges sliding past one another is no longer sufficiently present, because the cutting edges pass by one another without contact. This has the disadvantage that the cutting effect of the instrument is insufficient.

In a further embodiment of the known instrument, the scissor arms are interconnected with a link bolt about which the two arms are pivotal with respect to one another. Compared to the unconnected configuration, this embodiment represents an improvement with respect to guidance of the scissor arms during rotation, however, a spreading of the arms transversely to the cutting direction cannot be completely avoided with this linkage. In minimal invasive surgery, a miniaturised construction as far as possible is required, so that the scissor arms are often very thin. Since the scissor arms are only held together in the region of the link bolt, the link joint cannot always prevent a spreading of the scissor arms transversely to the cutting direction in the region of the distal ends of the arms. If the bolt is to hold the two scissor arms pressed closely to one another, it must be fixed to the scissor arms without play, which cannot be achieved in miniaturised construction with sufficient stability over longer duration.

A further problem results when the instrument, as foreseen in the known instrument, is to be configured not only for mechanical cutting, but also for bipolar coagulation of tissue. To allow bipolar coagulation, the two scissor arms must be configured as electrodes for receiving high frequency current. One scissor arm is connected to one pole of a high frequency voltage source and the other arm connected to the other pole, so that the two scissor arms carry different electric potentials. This in turn requires that the two scissor arms be insulated with respect to one another at least in the regions where they contact, so that current can flow to the distal ends of the scissor arms.

However, when the bolt also provides the pressure for urging the two scissor arms together, as in the known instrument, it must be form-fit or screw-connected to the two scissor arms, and therefore must be formed of metal. Problems of insulation then arise in the region of the link pin, such that a short circuit or leakage current can arise in this region. The current flow can then not be established to the distal ends of the scissor arms. Even if the metal bolt is provided with an insulation layer, leakage currents cannot be completely avoided. In addition, the insulation layer can wear off during use of the instrument, so that a sufficient insulation of the scissor arms cannot be reliably ensured.

Separable cutting elements are also known which are linked in a type of key-hole connection. This configuration also has the disadvantage that the scissor arms are not sufficiently guided and secured against spreading apart. A sufficient insulation of the scissor arms is also not reliably guaranteed.

The object of the present invention is therefore to provide an improved guidance of the scissor arms in a medical instrument of the mentioned type.

SUMMARY OF THE INVENTION

According to the present invention, an instrument for cutting and bipolar coagulating tissue in the human or animal body is provided, comprising:
 a shaft having a distal and a proximal end;
 a handle arranged at the proximal end;
 a first and a second scissor arm arranged at the distal end, the first and second scissor arms being pivotal about a stationary pivot axis arranged at the scissor arms, the two scissor arms being configured as electrodes to be supplied with high frequency current, wherein contacting regions of the two scissor arms are electrically insulated, and each of said first and second scissor arms comprising a cutting edge, said cutting edges slide across one another when pivoting said scissor arm,
 wherein at least one of said scissor arms comprises at least one bracket connected thereto which at least partially extends over an outer side of said other scissor arm.

The at least one bracket connected to one of the scissor arms and at least partially extending over the outside of the other scissor arm has the advantageous effect that the other scissor arm overlapped by the bracket is urged by the bracket toward the one scissor arm comprising the bracket or at least prevents a spreading apart of the two arms. Thus, it is ensured that the cutting edges are always in slide contact one another even when cutting harder tissue, especially vessels. The bracket thus provides the necessary retention of the two scissor arms, where the applied pressure achieved by the at least one bracket is more effective than the pressure achieved with the link bolt, because the bracket offers a larger pressing surface and in addition is dispaced from the pivot axis, as opposed to the known linkage. The pressing surface of the bracket is located closer to the distal end where the danger of spreading is the greatest.

In the instrument according to the present invention, not only is the mechanical cutting effect improved by the guidance, but, the scissor arms are additionally interconnected by a link, this link is relieved of stress, because the link no longer provides for holding the scissor arms together.

The link provided only serves the purpose of defining a pivot axis about which the two scissor arms are pivotal with respect to one another.

The suitability of the present instrument as a bipolar coagulation instrument together with a linked connection of the scissor arms is highly improved, because a link pin can be used for the linkage made of an electrically insulating material, for example ceramics, because this linkage need not provide the pressure holding the scissor arms together, but is substantially force free. In this manner, an electrical insulation of the two scissor arms can be reliably ensured in the region of the linkage.

A further advantage provided by the invention is that the scissor arms can be configured to be easily separated despite their guidance.

In accordance wit h the present invention, a bracket is to be understood as a portion of the scissor arm, independent of its form, arrangement or material, which starting from this scissor arm extends over the outside of at least a portion of the other scissor arm. Thus, this other arm is at least partially enclosed or clampable between the one scissor arm and this portion. It will be understood that the pivot motion of the scissor arms remains smooth, i.e. no substantially increased friction is caused by the bracket.

In a preferred embodiment, the at least one bracket comprises an extension in transverse direction to a longitudinal axis of the scissor arms such that it extends at least partially over the other scissor arm even in a maximally spread operational position of the scissor arms.

When the scissor arms are spread far apart, for example for cutting thick tissue or thicker vessels, the advantage is that a retaining effect of the scissor arms is achieved by the at least one bracket even when beginning the cut, so that a spreading or bending of the scissor arms transversely to the cutting direction is avoided even when starting the cut.

In a further preferred embodiment, the at least one bracket is wedge-shaped at a free end.

When the scissor arms assume a spread position in which the at least one bracket does not engage with the other scissor arm, this feature has the advantage that the introduction of the other scissor arm between the one scissor arm and the at least one bracket is improved. It is also made possible to urge the two scissor arms together with increasing pressure when closing the scissor arms along the inclination of the bracket.

Moreover, in a further preferred embodiment, the pivot axis is formed by a pin, which is releasable from at least one of the scissor arms.

This pin can thus be seated loosely in a respective bore of the one or the other scissor arm, without having to be press fit, screw connected or otherwise connected in fixed manner. In the present instrument for providing bipolar coagulation, this feature has the advantage that the pin can be made of an insulating material, for example ceramic or plastic, because the pin is not subjected to friction or even to shearing or compressive forces.

In a further preferred embodiment, the at least one bracket is arranged distally of the pivot axis.

This arrangement of the at least one bracket is of particular advantage, because the effective cutting region of the scissor arms is also at the distal side of the pivot axis and the tendency of the arms to spread apart transversely to the cutting direction is the largest there.

Additionally or alternatively, the at least one bracket can be arranged proximally of the pivot axis.

Particularly preferred is the provision of at least one bracket at the distal side and at least one further bracket at the proximal side of the pivot axis.

In the configuration with at least one bracket at the distal side and at least one bracket at the proximal side of the pivot axis, the mentioned pivot connection between the two scissor arms with the pin is completely relieved of stress. This is because the forces acting on the scissor arms at the distal side of the pivot axis and also the forces acting on the scissor arms at the proximal side of the pivot axis, which would cause a spreading of the scissor arms transversely to the cutting direction or transversely to the axial direction of the arms, are taken up by the two brackets and thus not by the link pin.

In a further preferred embodiment, each scissor arm comprises at least one bracket, and/or one of the scissor arms or both of the scissor arms comprise at least two axially spaced brackets.

In a further preferred embodiment, the at least one bracket is formed integrally with the associated scissor arm.

The stability of the instrument in the region of the scissor arms is further improved with this feature.

In another preferred embodiment, the at least one bracket becomes disengaged with the other scissor arm in a spread position going beyond the maximally spread operational position and the scissor arms in this spread apart position are separable from one another.

The separability of the scissor arms has the advantage of easier cleaning of the instrument in the region of the scissor arms after use. In particular, remaining pieces of tissue or blood collected between the scissor arms can be easily and completely removed. The separability of the scissor arms in this configuration is also particularly simple to manipulate, because the scissor arms only need to be opened to the mentioned spreading position until the at least one bracket releases the other scissor arm. A particularly simple separability of the two scissor arms also results in combination with the abovementioned configuration, where the two scissor arms are pivotal relative to one another about a pivot axis, the pivot axis being formed by a pin which is releasable from at least one of the scissor arms. In the operational state, the scissor arms are secured to one another against undesired separation, so that no further securement means are needed in the region of the pivot axis or the pivot pin.

In a further preferred embodiment, the scissor arms comprise an elastic bending portion at their respective proximal ends, where the bending portions are pushed together by axially shifting the tubular shaft over the bending portions. The scissor arms are thereby pivoted from their spread position into their closed position and vice versa.

This type of actuation for opening and closing the scissor arms, which is known from U.S. Pat. No. 5,334,198, leads to a constructively simple actuator mechanism for the instrument.

As already mentioned, the scissor arms are configured to be electrodes supplied with high frequency electric current. In this manner, the instrument is suited not only for mechanical cutting but also for coagulation as a bipolar coagulation instrument.

The regions of the one scissor arm and the regions of the other scissor arm which contact one another are electrically insulated so that the present instrument is suitable as a bipolar coagulation instrument. Bipolar coagulation has the advantage that the current flow is limited to the region between the scissor arms having different potentials.

Further advantages can be taken from the following description and the attached drawings. It will be understood that the above-mentioned features and those to be discussed below are applicable not only in the given combinations, but may be present in other combinations or taken alone without departing from the scope of the present invention.

An embodiment of the invention is illustrated in the drawings and will be discussed in more detail in the following description.

BRIEF DESCRIPTION OF THE DRAWINGS

FIG. 2 shows a perspective view from the front of the distal region of the instrument in enlarged scale where the scissor arms of the instrument are in their closed position.

FIG. 3 shows a perspective view from behind of the distal region of the instrument in a position rotated by 180° compared to FIG. 2, where the scissor arms of the instrument are shown in their maximally spread operational position.

DETAILED DESCRIPTION OF A PREFERRED EMBODIMENT

Figure 1:
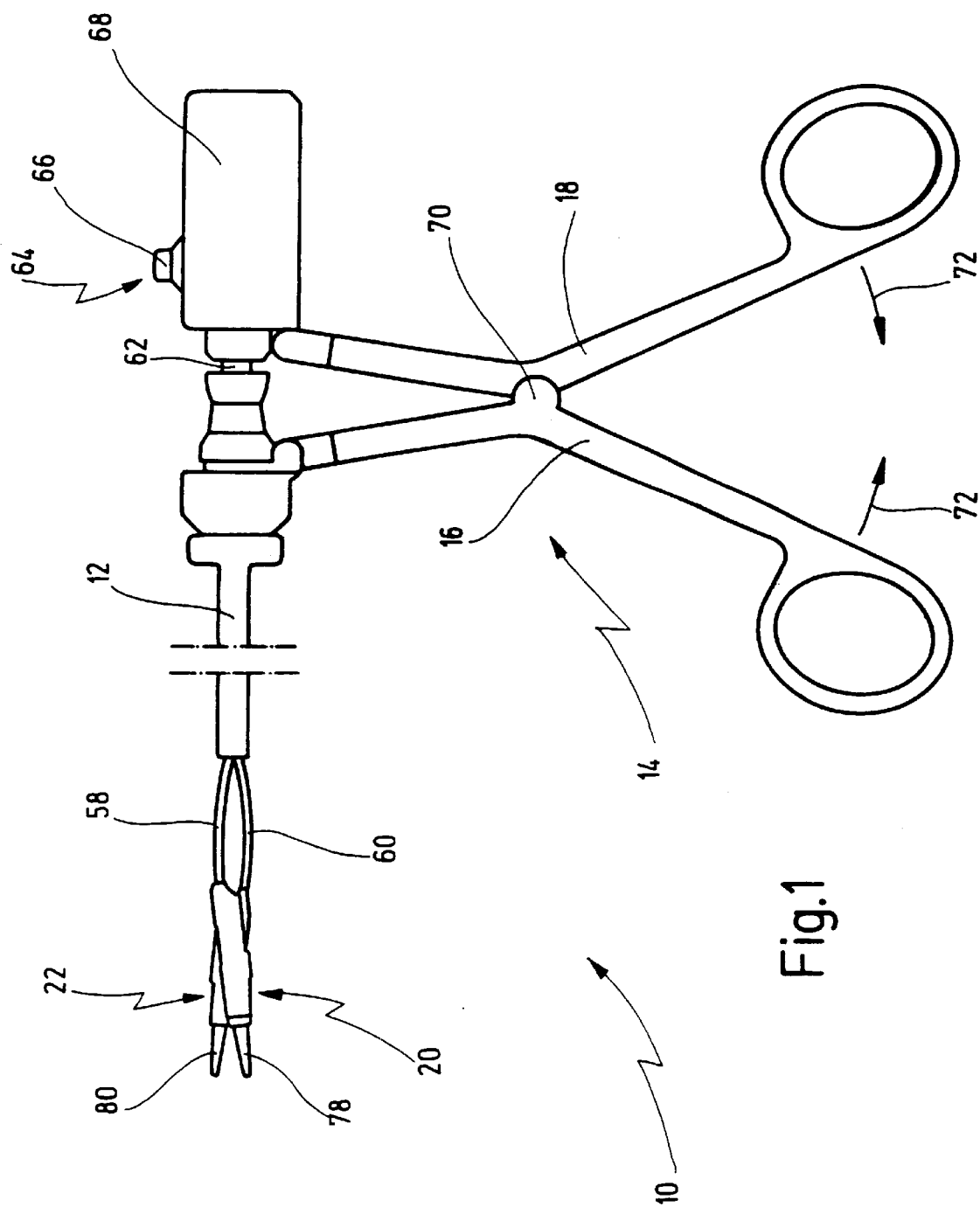
FIG. 1 shows a side view of a medical instrument in complete illustration.

A medical instrument for cutting tissue in the human or animal body is shown in FIG. 1 and designated with the numeral 10, which is used in minimally invasive surgery. Details of the instrument 10 are shown in the FIGS. 2 to 7. Hard or soft tissue can be mechanically cut or coagulated in a bipolar procedure with the instrument 10.

The instrument 10 according to FIG. 1 generally comprises a tubular shaft 12, a handle 14 with a first grip 16 and a second grip 18 as well as a first scissor arm 20 and a second scissor arm 22, where the first scissor arm 20 and the second scissor arm 22 are pivotal with respect to one another. The tubular shaft 12 is arranged between the distal scissor arms 20, 22 and the proximal handle 14. The interaction of the handle 14 with the tubular shaft 12 and the scissor arms 20, 22 will be described in more detail below.

With reference to FIGS. 2 to 7, the configuration of the scissor arms 20, 22 will be described in more detail. The first scissor arm 20 and the second scissor arm 22 are formed to be straight in their axial direction, where the scissor arms 20, 22 however could also be curved or bent in the axial direction. A bent configuration can further improve the mechanical cutting effect of the instrument 10.

The first scissor arm 20 comprises a first cutting edge 24 while the second scissor arm 22 comprises a second cutting 26. The cutting edges 22, 24 slide across one another when pivoting the scissor arms 20, 22. The scissor arms 20, 22 are shown in FIG. 3 in their maximally spread operational position, from which a cutting operation with the instrument begins, and are shown in FIG. 2 in their closed position, i.e. after a cut has been carried out.

As discussed in more detail below, the scissor arms 20, 22 are resiliently biased to the open position illustrated in FIG. 3, i.e. scissor arms 20, 22 automatically take on the maximally spread operational position shown in FIG. 3.

The first scissor arm 20 comprises a first bracket 28, where the bracket 28 is connected to the first scissor arm 20, namely integrally connected thereto in the present embodiment. The first bracket 28 extends to at least partially cover the outside of the second scissor arm 22 as shown in FIG. 2. The outside means that the first bracket 28 extends over the outer side 30 of the second scissor arm 22, which opposes the first scissor arm 20, and therefore holds the scissor arms 20, 22 together.

The first bracket 28 has an approximately L-form, where a first shank 32 of the first bracket 28 runs approximately perpendicular to the outer side 30 and therefore perpendicular to the main plane of the scissor arms 20, 22. A second shank 34 runs parallel to the outer side 30. The first shank 32 and the second shank 34 are disposed approximately perpendicular to one another and have the form of a rectangle.

The first bracket 28 has an extension in the transverse direction to the axis of the scissor arms 20, 22, such that it still at least partially extends over the second scissor arm 22 up to the maximally spread operational position of the scissor arms 20, 22 as shown in FIG. 3.

The second scissor arm 22 is therefore urged against the first scissor arm 20 by the first bracket 28, so that a spreading of the scissor arms 20, 22 in the transverse direction to the axial direction or transversely to the cutting direction is avoided, namely over the entire pivot range of the scissor arms 20, 22 between the maximally spread operational position in FIG. 3 and the closed position in FIG. 2.

Figure 7:
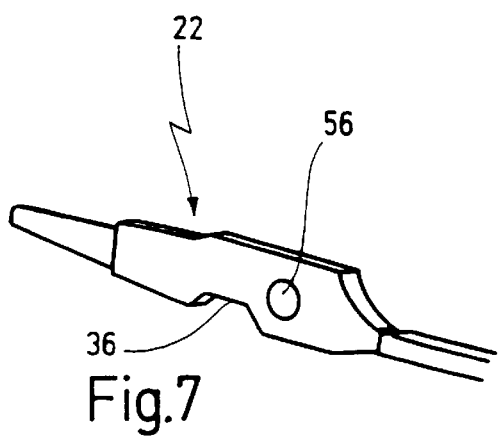
FIG. 7 shows the second scissor arm of the instrument illustrated alone.

As is best seen in FIG. 7, the second scissor arm 22 is provided with a recess 36 in the region of the first shank 32 of the first bracket 28, in which the first shank 32 comes to rest in the closed position of the scissor arms 20, 22 shown in FIG. 2. Thus, an undesired opening of the scissor arms 20, 22 is avoided through the provision of the first bracket 28.

The first scissor arm 20 further comprises a second bracket 38, which is also connected to the first scissor arm 20, and which also extends to at least partially cover the second scissor arm 22. The second bracket 38 is also approximately L-shaped and accordingly comprises a first shank 40 and a second shank 42, which correspond to the first shank 32 and the second shank 34 of the first bracket 28. The form of the first shank 40 and the second shank 42 of the second bracket 38 differ from the form of the first shank 32 and the second shank 34 of the first bracket 28, however, the form of the brackets 28 and 38 is not critical.

Figure 4:
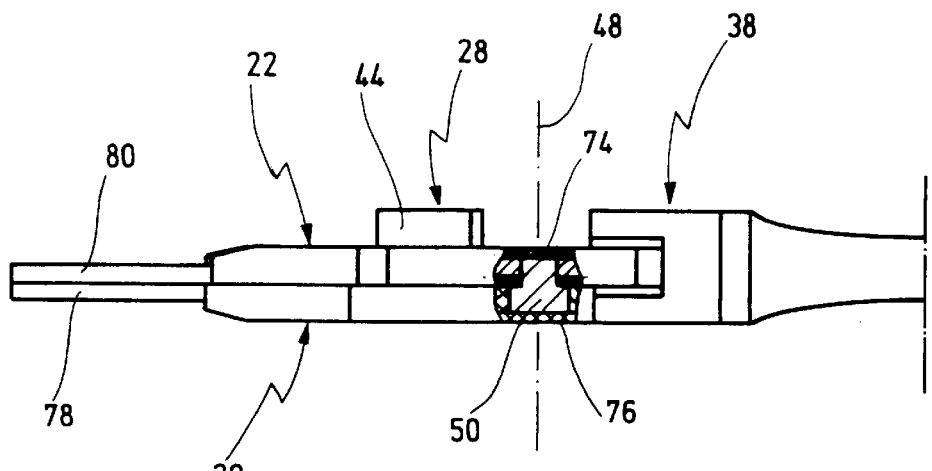
FIG. 4 shows a plan view of the distal region of the instrument in partially cut away illustration.
Figure 5:
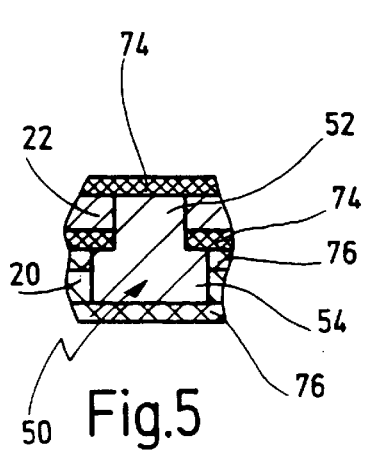
FIG. 5 shows a longitudinal cross section of FIG. 4 in a further enlarged scale.
Figure 4A:
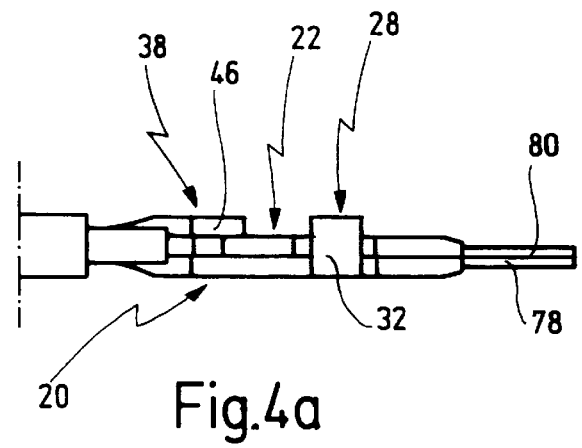
FIG. 4a) shows a view of the distal region from below in a smaller scale compared to FIG. 4.
Figure 6:
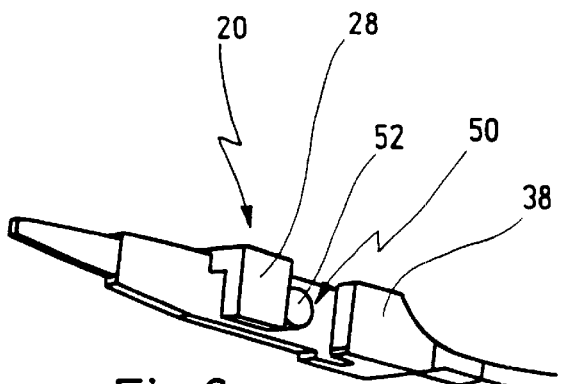
FIG. 6 shows the first scissor arm of the instrument illustrated alone.

The first bracket 28 and the second bracket 38 extend over the second scissor arm 22 from opposing sides, i.e. a free end 44 of the first bracket 28 and a free end 46 of the second bracket 38 lie opposed to one another with respect to the axis of the scissor arms 20, 22 as can be seen from FIGS. 4 and 4a).

According to FIG. 4, the first scissor arm 20 and the second scissor arm 22 are pivotal with respect to one another about a stationary pivot axis 48. As shown in FIG. 4, the first bracket 28 is arranged at the distal side of the pivot axis 48 and the second bracket 38 is arranged at the proximal side of the pivot axis 48. The scissor arms 20, 22 are held together at the proximal side of the pivot axis 48 by the second bracket 38, while the first bracket 28 holds the scissor arms 20, 22 together at the distal side of the pivot axis 48.

The pivot axis 48 is formed by a pin 50. The pin 50 is cylindrically symmetrical on the whole. The pin 50 has a portion 52 having a smaller diameter and a portion 54 with a larger diameter. The portion 54 with the larger diameter is placed in a bore in the first scissor arm 20, while the portion 52 of smaller diameter is placed in a corresponding bore 56 of the second scissor arm 22. The pin 50 is loosely received in the first scissor arm 20 as well as in the second scissor arm 22, i.e. the pin 50 can be removed both from the first and also from the second scissor arm. However, the pin 50 can be placed in the first scissor arm 20 to be non-removable, while being loosely placed in the second scissor arm 22.

In operation of the instrument 10, the scissor arms 20, 22 can be pivoted with respect to one another about the pin 50. The loose connection of the pin 50 with the scissor arms 20, 22 is made possible by the provision of the at least one bracket 28, in the present case by the first bracket 28 and the second bracket 38. In operation, these brackets hold the scissor arms 20, 22 inseparably together and pressed onto one another. The pin 50 only has the function of defining a stationary pivot axis 48. In the separated illustration of the first scissor arm 20 in FIG. 6, the smaller diameter portion 52 of the pin 50 is seen, while the bore 56 into which the portion 52 of the pin 50 is inserted is shown in FIG. 7. The scissor arms 20, 22 cross over one another at the pin 50. The pin 50 is not visible from the outside in the assembled condition of the scissor arms 20, 22.

The first scissor arm 20 and the second scissor arm 22 each comprise an elastic bending portion 58, 60 at their proximal ends. The bending portions 58, 60 are configured in the form of leaf springs, which take on an outwardly curved configuration in their rest position. The scissor arms 20, 22 are connected to an inner tube 62 through the bending portions 58, 60, which in turn is releasably locked to a housing 68 at the proximal end of the instrument 10 by a locking mechanism 64 having a button 66. The housing 68 is also configured as a socket housing for connecting an electric cable communicating with a high frequency voltage source.

Initially however, the function of the instrument 10 for mechanically cutting tissue will be described. The first grip 16 and the second grip 18 of the handle 14 are movable relative to one another through a joint 70. The grip 16 is fixed to the tubular shaft 12. The tubular shaft 12 in turn is axially shiftable relative to the inner tube 62 and therefore to the bending portions 58, 60 of the scissor arms 20, 22.

By pressing the grips 16, 18 together in the direction of the arrows 72, the tubular shaft 12 is shifted axially to the distal end, starting from the operational position shown in FIGS. 1 or 3, which represents the maximally spread operational position of the scissor arms 20, 22. In this operation, the tubular shaft glides over the bending portions 58, 60 of the scissor arms 20, 22 causing these to move into the closed position illustrated in FIG. 2, whereby the cutting edges 24, 26 slide across one another. The brackets 28, 38 ensure the necessary pressing force on the scissor arms 20, 22 toward one another and therefore on the cutting edges 24, 26 when cutting tissue or vessels. The pin 50 forming the pivot axis 48 remains substantially force free and only provides for the definition of the pivot axis 48.

As mentioned above, the instrument 10 is not only suited for mechanical cutting, but can also be employed for bipolar coagulation of tissue. For this purpose, the scissor arms 20, 22 are formed as electrodes to be supplied with high frequency current, where the first scissor arm 20 and the second scissor arm 22 are electrically insulated from one another and can be connected to the first and second poles of a high frequency voltage source. The scissor arms 20, 22 including the brackets 28, 38 are made of metal, where the scissor arms 20, 22 are completely surrounded by insulation 74, 76 in the regions where they contact. The brackets 28, 38 are also electrically insulated. Only the distal ends 78, 80 of the scissor arms 20, 22 are bare metal. Power is supplied to the distal ends 78, 80 of the scissor arms 20, 22 from corresponding contacts (not shown) in the housing 68 through wires (not shown) in the inner tube 62, then through the bending portions 58, 60 which are also insulated on the outside, an d finally to the distal ends 78, 80 of the scissor arms 20, 22.

The pin 50 is made of an insulating material, for example a ceramic or synthetic material, however, can be made of metal with an insulating coating.

In the maximally spread operational position shown in FIGS. 1 and 3, where the distal ends 78, 80 of the scissor arms 20, 22 are not in contact, bipolar coagulation can be carried out by switching on the high frequency current either before cutting the tissue or after cutting. The current flow is concentrated to the region between the distal ends 78, 80 of the scissor arms 20, 22. A short circuit or leakage current in the region of the pin 50 does not occur because the pin 50 is formed of an insulating material, which is possible because the pin 50 need not apply the force pressing the scissor arms 20, 22 together.

An embodiment of the configuration and arrangement of the first bracket 28 and the second bracket 38 is described above, although it will be understood that the arrangement and configuration of the brackets 28, 38 are not limited thereto. For example, only one bracket can be provided or more than two brackets can be provided or for example both scissor arms can be provided with at least one bracket. Furthermore, the free end 44 or 46 of the brackets 28 and 38 can be sloped to become wedge-shaped.

In a further embodiment of the instrument 10, the first scissor arm 20 and the second scissor arm 22 are separable from one another as will be described in the following with reference to FIGS. 8*a*) to *c*). After first removing the assembly consisting of the inner tube 62, the bending portions 58, 60 and the scissor arms 20, 22 from the housing 68 and therefore from the handle 14 by releasing the locking mechanism 64, the bending portions 58, 60 are removed from the inner tube 62.

Figure 8:
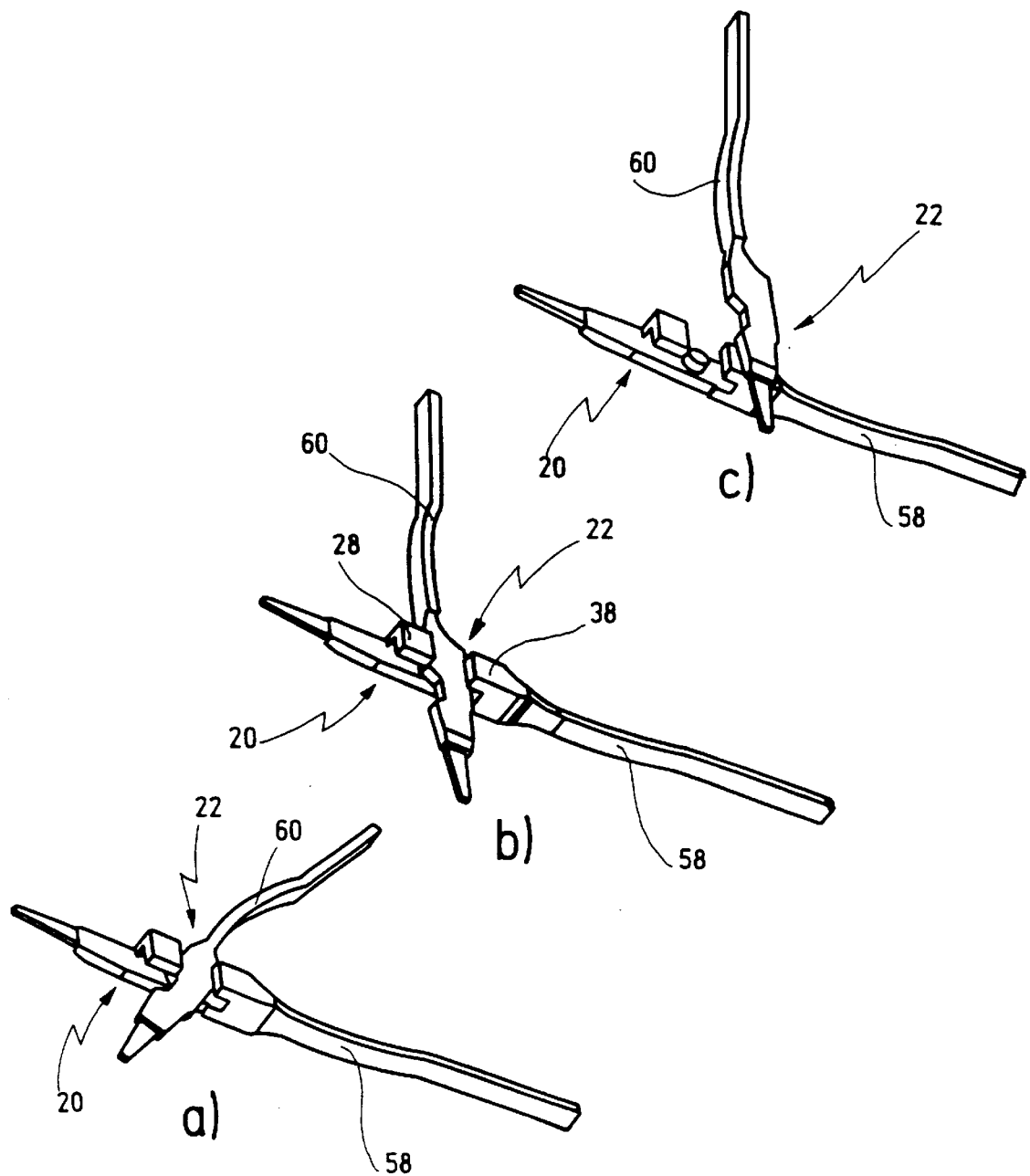
FIG. 8a) to c) show the function of separating or assembling the two scissor arms.

The second scissor arm 22 can then be pivoted relative to the first scissor arm 20 beyond the maximally spread operational position shown in FIG. 3 about the pivot axis 48 formed by the pin 50 as is shown in FIG. 8*a*). The second arm 22 as shown in FIG. 8*b*) is then pivoted relative to the first scissor arm 20 to the extent that the first bracket 28 and the second bracket 38 no longer engage with the second scissor arm 22. The first bracket 28 and the second bracket 38 are axially spaced corresponding to the width of the second scissor arm 22. In this position, the first scissor arm 20 and the second scissor arm 22 disposed approximately perpendicular to one another.

In this position, the second scissor arm 22 can then be lifted from the first scissor arm 20, because the pin 50 is loosely inserted into the second scissor arm 22. FIG. 8*c*) illustrates first scissor arm 20 having been separated from the second scissor arm 22. For reassembling the instrument 10, the corresponding steps are performed in reverse sequence.

What is claimed is:

1. Medical instrument for cutting and bipolar coagulating tissue in the human or animal body, comprising:

a shaft having a distal and a proximal end;

a handle arranged at said proximal end;

a first and a second scissor arm arranged at said distal end, said first and second scissor arms being pivotal about a stationary pivot axis arranged at said scissor arms, said two scissor arms further being configured as electrodes to be supplied with high frequency current, wherein contacting regions of said two scissor arms are electrically insulated, and each of said first and second scissor arms comprising a cutting edge, said cutting edges slide across one another when pivoting said scissor arms, wherein at least one of said scissor arms comprises at least one bracket connected thereto which at least partially extends over an outer side of said other scissor arm.

2. The instrument of claim 1, wherein said at least one bracket comprises an extension in transverse direction to a longitudinal axis of said scissor arms, such that it at least partially extends over said other scissor arm even in a maximally spread operational position of said first and second scissor arms.

3. The instrument of claim 1, wherein said at least one bracket is wedge-shaped at a free end thereof.

4. The instrument of claim 1, wherein said pivot axis is formed by a pin releasable from at least one of said scissor arms.

5. The instrument of claim 1, wherein said at least one bracket is arranged distally of said pivot axis.

6. The instrument of claim 1, wherein said at least one bracket is arranged proximally of said pivot axis.

7. The instrument claim 1, wherein said at least one bracket is arranged distally and at least one further bracket is arranged proximally of said pivot axis.

8. The instrument of claim 1, wherein said first and second scissor arms each comprise at least one bracket.

9. The instrument of claim 1, wherein at least one of said scissor arms comprises at least two brackets spaced axially from one another.

10. The instrument of claim 1, wherein said at least one bracket is integrally connected with said associated scissor arm.

11. The instrument of claim 1, wherein said at least one bracket disengages with said other scissor arm in a spread position going beyond a maximally spread operational position and wherein said first and second scissor arms are separable from one another in this spread position.

12. The instrument of claim 1, wherein said scissor arms comprise an elastic bending portion at their respective proximal ends, said shaft being axially shiftable and tubular and wherein said bending portions are compressed by said shaft when sliding said tubular shaft over said bending portions, whereby said scissor arms are pivoted to their closed position from their spread position and vice versa.

* * * * *